United States Patent [19]

Anspach, Jr. et al.

[11] Patent Number: 5,405,348

[45] Date of Patent: Apr. 11, 1995

[54] SURGICAL CUTTING INSTRUMENT

[76] Inventors: William E. Anspach, Jr., 4500 Riverside Dr., Palm Beach Gardens, Fla. 33410; Eddy H. Del Rio, 11413 52nd Rd. N., Royal Palm Beach, Fla. 33411

[21] Appl. No.: 17,033

[22] Filed: Feb. 12, 1993

[51] Int. Cl.⁶ ............................................. A61B 17/32
[52] U.S. Cl. ................................... 606/80; 606/79; 606/170; 606/180
[58] Field of Search ................ 606/80, 81, 79, 76, 606/96, 104, 167, 170, 180, 84, 85; 128/750, 751, 753, 755; 433/165, 166; 408/199, 226, 204, 205

[56] References Cited

U.S. PATENT DOCUMENTS

| | | | |
|---|---|---|---|
| 3,071,861 | 1/1963 | Saffir | 433/132 |
| 3,732,858 | 5/1973 | Banko | 128/753 |
| 4,456,010 | 6/1984 | Reimels et al. | 606/173 |
| 4,568,642 | 2/1986 | DeForrest et al. | 433/132 |
| 4,844,064 | 7/1989 | Thimsen et al. | 606/80 |
| 4,856,503 | 8/1989 | Schelhas | 606/80 |
| 4,976,720 | 12/1990 | Machold et al. | 606/194 |
| 5,084,052 | 1/1992 | Jacobs | 606/79 |
| 5,222,956 | 6/1993 | Waldron | 606/80 |

FOREIGN PATENT DOCUMENTS

| | | | |
|---|---|---|---|
| 184393 | 7/1966 | U.S.S.R. | 606/80 |
| 1124938 | 11/1984 | U.S.S.R. | 606/80 |

*Primary Examiner*—Stephen C. Pellegrino
*Assistant Examiner*—Guy V. Tucker
*Attorney, Agent, or Firm*—Jack N. McCarthy

[57] ABSTRACT

A surgical drilling instrument comprises a nose body attached to a power source, the nose body having a shaft support tube extending therefrom around a drive shaft with a cutter. The forward end of the shaft support tube has a bearing construction supporting the drive shaft. A water supply is directed into the annular space between the shaft support tube and the drive shaft, and is further directed over the bearing construction onto the cutter. This (1) aids in supporting the drive shaft; (2) cools the cutter; and (3) flushes the cutting area.

12 Claims, 5 Drawing Sheets

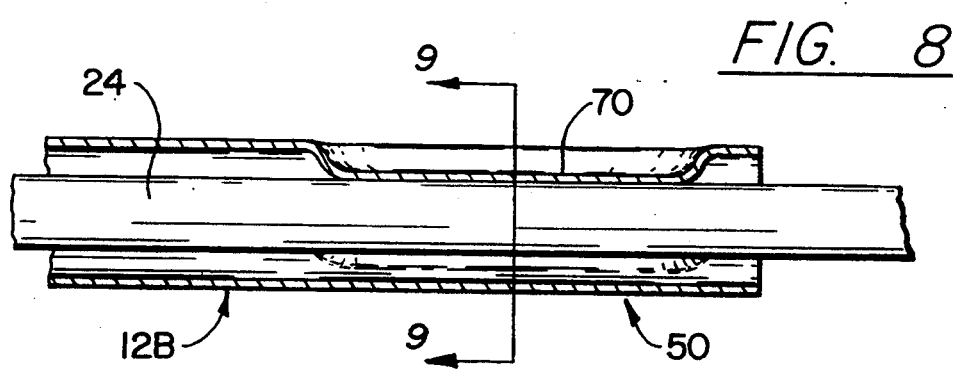
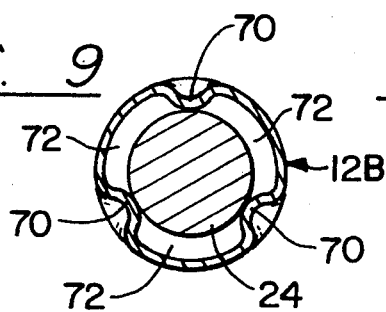
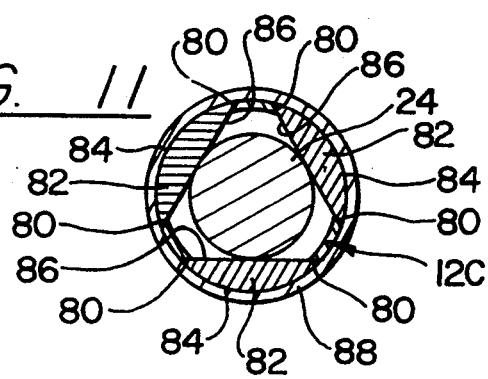
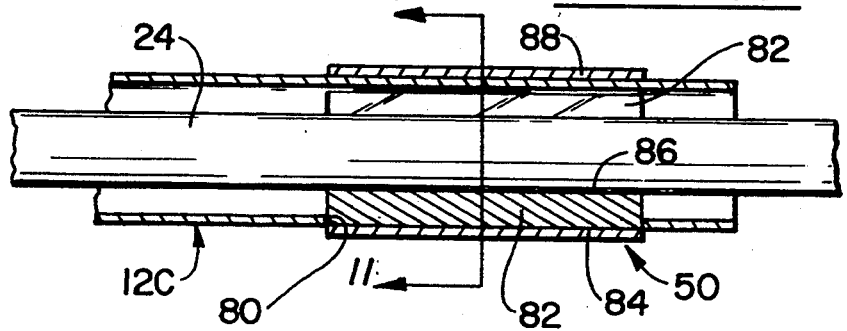

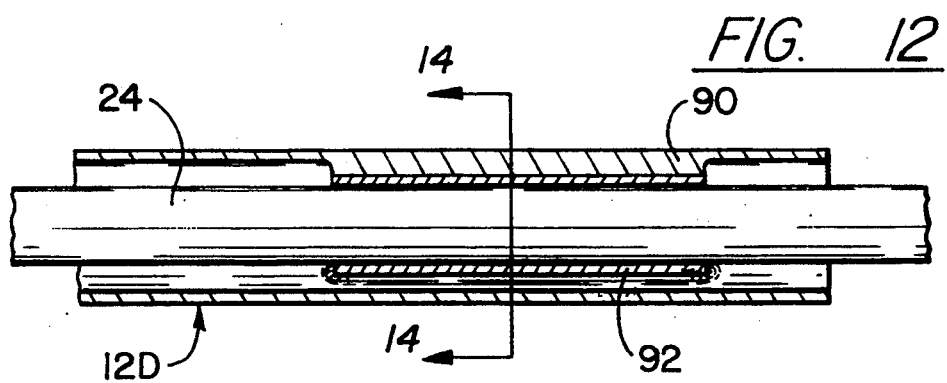
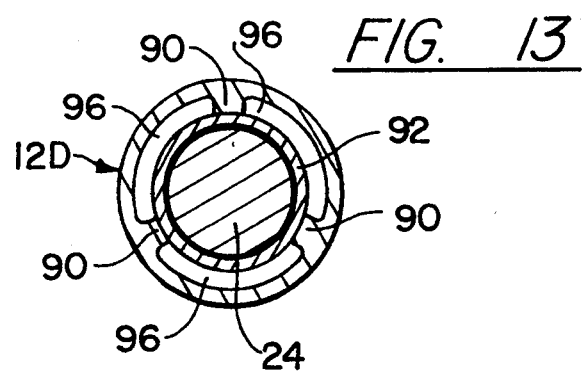

SURGICAL CUTTING INSTRUMENT

TECHNICAL FIELD

This invention relates to a device for supporting a high speed cutter and cutter shaft attached to a power tool.

BACKGROUND ART

Surgical drills and cutters, such as burrs, in common use today, run at relatively high RPM, in the range of 25 thousand to 100 thousand RPM. Rotating shafts in these instruments have been contained in ball or roller bearings. In view of the high RPM and because of the use of bearings having metal contact, it is possible to permit metal particles to pass into the patient. In using ball or roller bearings, the diameter of the surgical drilling instrument was limited to the diameter of the tube that would contain these bearings. Many surgical procedures are performed under very high magnification which allows the surgeon to be much less invasive in that the wound can be quite small. If the wound is small and one is limited to a large diameter surgical instrument, his vision is limited. In other instances, such as that found with failed artificial hip joints, it is necessary for a very small cutter to remove the bone ingrowth between a metal implant and the surrounding bone. If an implant ever has to be removed, which is metal covered with a porous substance into which the patient's bone grows, this can be virtually an impossible task. One method is by cutting away the region where the bone has grown into the implant using chisels and hammers.

DISCLOSURE OF INVENTION

It is an object of this invention to provide a cutter and cutter shaft with a small diameter shaft support tube to be able to enter a small wound and allow the surgeon to have ample vision.

It is another object of the invention to permit a longer cutter shaft by providing a fluid bearing which can be used without ball, or roller, bearings. A nose piece, or nose cone, is constructed to be connected at one end to a power tool, such as the ANSPACH 65K, and have a cutter shaft extend from the other end surrounded by a shaft support tube, said shaft support tube having a flow of liquid therethrough during operation to provide bearing support and damping throughout for the cutter shaft with a fixed bearing construction at the free end having a high density and low coefficient of friction, provision at the fixed bearing being made for directing the flow of liquid onto the cutter for cooling and flushing.

It is a further object of the invention to provide a drilling instrument having very high operating RPM (approximately 80K) with high stability, minimal vibration, and minimum cutter shaft wear.

It is another object of this invention to have liquid coaxial flow around the cutter shaft to provide bearing support and damping.

It is a further object of the invention to provide liquid cooling for thee positive bearing construction at the end of the shaft support tube between the shaft support tube and the cutter shaft with liquid being directed at the cutter for cooling it. Said positive bearing construction provides flow restriction therethrough to maintain liquid in said annular passageway for support and damping of the cutter shaft.

It is another object to provide the maximum accessibility and visibility into the area being operated on, while reducing the possibility of metal fragment invasion.

It is a further object of this invention to fix the cutter as close as possible to the end of the shaft support tube to prevent a whipping of the cutter shaft. Provisions are made by a radial opening in the nose piece into the rear recess to tighten a collet on a power tool while the power tool driving shaft is held secure to provide relative tightening movement of the collet while permitting the closest positioning of the cutter to the free end of the shaft support tube.

BRIEF DESCRIPTION OF DRAWINGS

FIG. 8 is a view similar to FIG. 3 of a modified positive bearing arrangement wherein said shaft support tube remains cylindrical with the shaft support tube bent inwardly at three locations to form three fixed bearing members providing bearing contact;

FIG. 9 is a view taken on the line 9—9 of FIG. 8;

FIG. 10 is a view similar to FIG. 8 of a modified positive bearing arrangement wherein said shaft support tube has cut-out portions around the periphery to receive inserts held in position by a holding sleeve to form fixed bearing members providing bearing contact;

FIG. 11 is a view taken on the line 11—11 of FIG. 10;

FIG. 12 is a view similar to FIG. 5 of a modified positive bearing arrangement wherein said shaft support tube remains cylindrical with support members extending inwardly to support a cylindrical sleeve bearing around the cutter shaft;

FIG. 13 is a view taken on the line 13—13 of FIG. 12; and

BEST MODE FOR CARRYING OUT THE INVENTION

Figure 2:
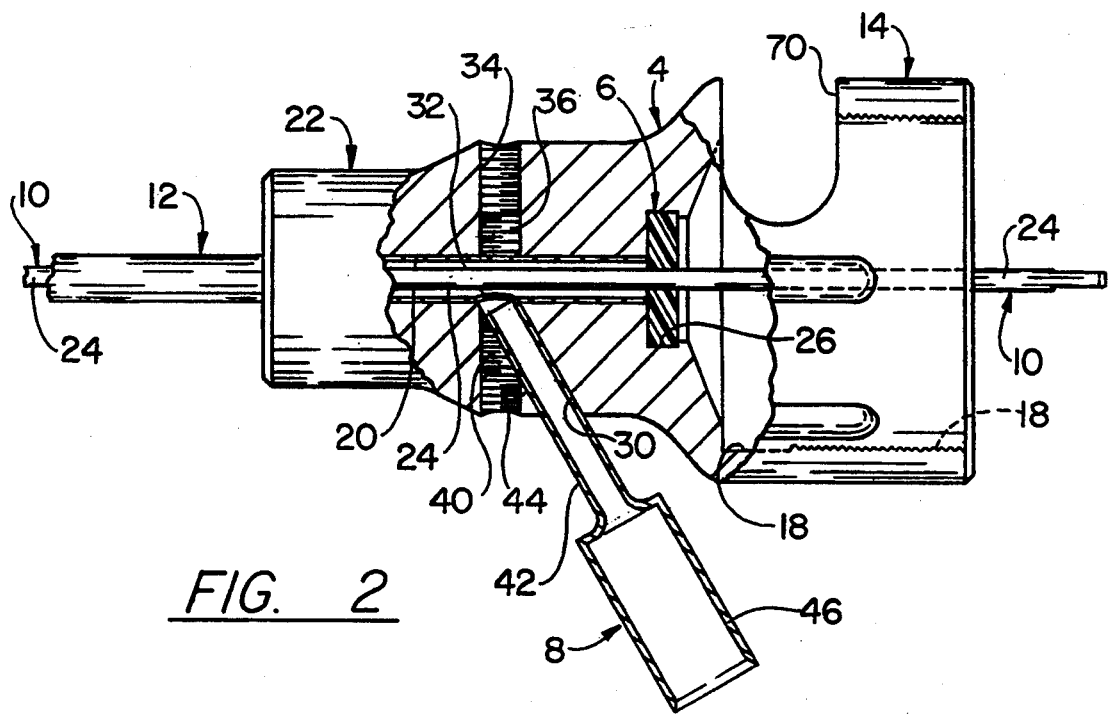
FIG. 2 is an enlarged view of the nose piece in partial section showing the relationship of the cutter shaft and shaft support tube with the seal and liquid input tube.
Figure 1:
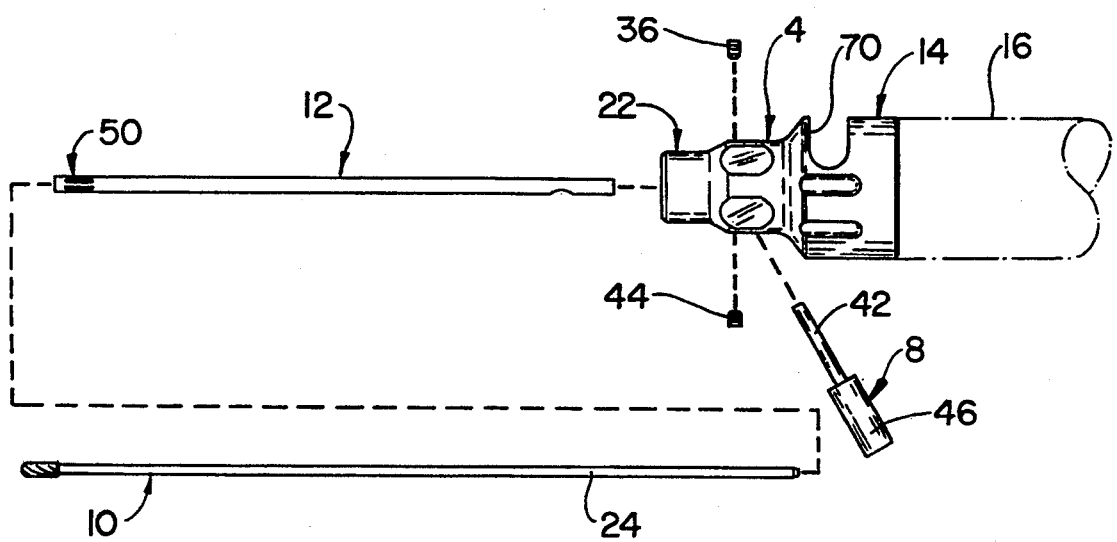
FIG. 1 is an exploded view of the surgical drilling instrument showing the relationship of the cutter and cutter shaft assembly, cutter shaft support tube, and nose piece.

Referring to FIGS. 1 and 2, a surgical drilling instrument 2 is shown with the following six main parts:
(1) a nose piece, or body member, 4;
(2) a nose piece seal 6;
(3) a nose piece liquid input tube 8;
(4) a cutter and cutter shaft assembly 10;
(5) a shaft support tube 12; and
(6) a bearing means 50 between a free end of shaft support tube 12 and the cutter and cutter shaft assembly 10. Nose piece 4 has a rearward end 14 formed in cylindrical-like fashion to be connected to a power source 16 (shown in phantom in FIG. 1) forming an extension thereof so as to be held in the hand, or hands, of a surgeon for surgical use. An ANSPACH 65K is a commercially available motor, driven by either sterile air or nitrogen and having a cylindrical-like shape.

While the nose piece 4 is shown having an internally threaded recess 18 to be attached to a power source 16, other connecting means can be used. An opening 20 extends from the forward end 22 of the nose piece 4 into the recess 18 to slidably receive one end of the shaft support tube 12. The seal 6 is provided at the rear end of the nose piece 4 in a countersunk opening 26 at the bottom of the recess 18 to position the end of the shaft support tube 12 and to receive the cutter shaft 24 placed in the shaft support tube 12 and seal it with the nose piece 4. This seal 6 can be a single ring, or a plurality of rings fixed in place. Teflon has been used. They are shown fixed by being swaged in place; the bottom surface of the recess 18 is formed over the outer edge of the seal 6. Other seal attachments can be used.

The nose piece 4 has an opening 30 cut through at an angle from the exterior surface to a mid-point of the opening 20, said opening 30 providing for the input of a liquid to the opening 20. Shaft support tube 12, with its inner end positioned against the seal 6, has an opening 32 therein which is aligned with the inner end of the opening 30. A tapped hole 34 is placed through a mid-portion of the nose piece 4 to the opening 20 to receive a threaded holding member 36. When the shaft support tube 12 is in place, this threaded holding member 36 is tightened to fix the shaft support tube 12 in place with the opening 32 aligned with opening 30.

Figure 14:
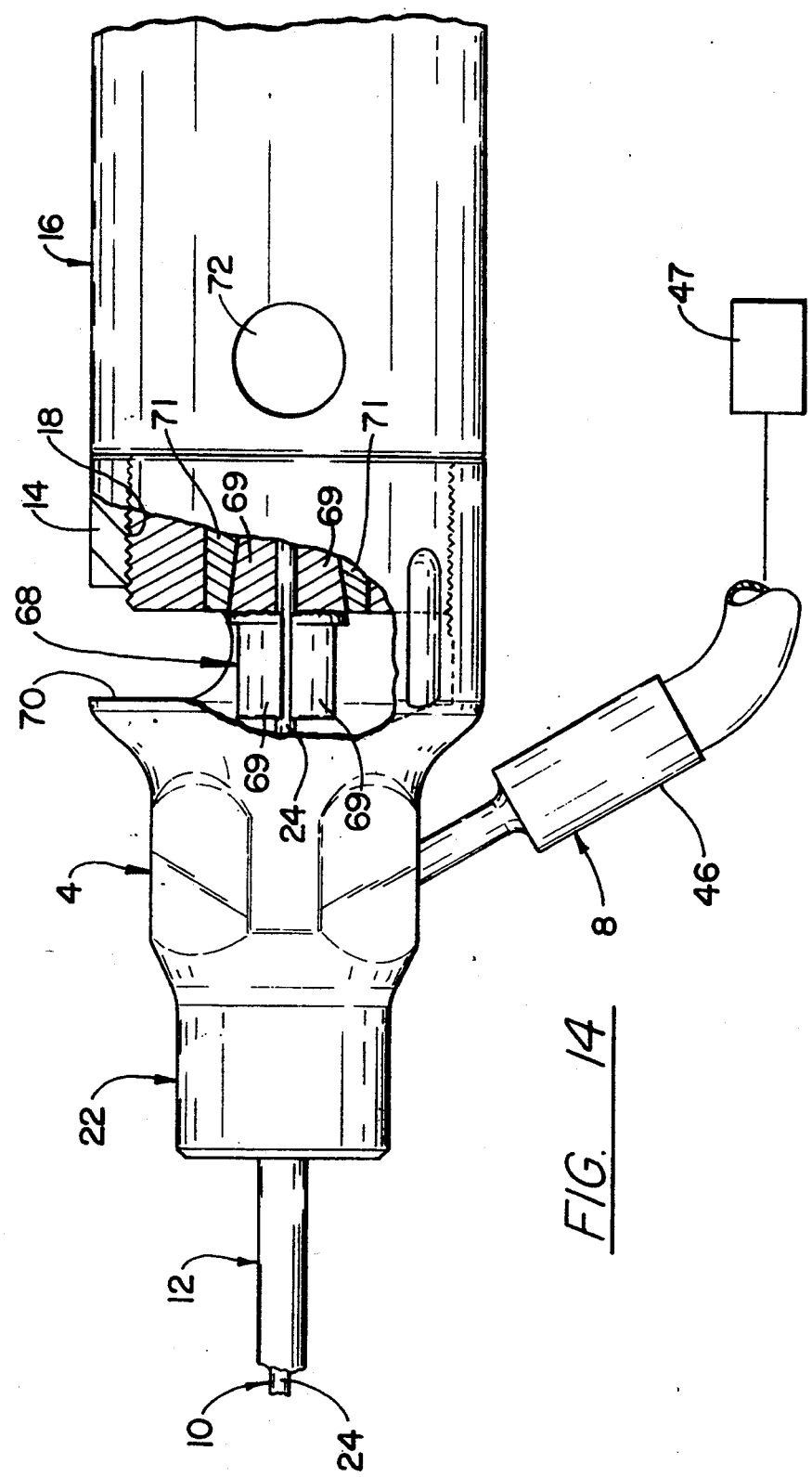
FIG. 14 is a view similar to FIG. 2 showing the relationship between the peripheral opening in the nose piece and the collet of the power source.

A second tapped hole 40 is placed through a mid-portion of the nose piece 4 to intercept the opening 30. A liquid input tube 8 has a forward tubular section 42 adapted to be slidably engaged in the opening 30, said forward tubular section 42 extending to the shaft support tube 12 in line with the opening 32. A threaded holding member 44 is placed in the tapped hole 40 to be tightened against the forward tubular section 42 to hold it in place. The liquid input tube 8 has a rearward tubular section 46 adapted to receive a supply 47 (see FIG. 14) of liquid under pressure to provide for bearing support and cooling. The supply 47 of liquid under pressure can be controlled to achieve proper flow.

The forward end of the cylindrical-like shape of the power source 16 threaded into the rearward end 14 of nose piece 4 has a collet 68, with jaws 69, mounted therein which extends from the center thereof for holding and driving shaft 24 of the cutter 25 and cutter shaft assembly 10 (see FIG. 8). The collet 68 is connected to a collet receptacle 71 on the output shaft of the power source 16 by cooperating threads on each member. As the collet 68 is threaded into its mating threads in the collet receptacle 71 the jaws 69 are moved together by the mating tapered surfaces between the collet 68 and receptacle 71. A peripheral opening, or window, 70 extends through the rearward end 14 of the nose piece 4 to be radially in line with the collet 68 so that the jaws 69 can be held, as by a wrench extending through said opening 70, to rotate the collet 68 to open and close the jaws 69 while the output shaft of the power source 16 is held fixed. As the wrench reaches the extent of its arcuate movement in peripheral opening 70, it will rotate the nose piece 4 until the collet 68 has a firm hold on the end of cutter shaft 24. A button 72 is provided on the power source 16 to push into contact with a recess on its output shaft to hold its output shaft fixed. Other holding means can be used. This permits an operator to mount the nose piece 4 on the power source 16 at a desired position, then properly fix the cutter 25, having the proper length of the cutter shaft 24, a desired distance from the end of the shaft support tube 12, by tightening the jaws 69 of collet 68 through the peripheral opening 70.

The peripheral opening 70 only permits approximately a 120° rotation of a wrench to tighten the collet. To provide for a tight connection of collet 68 on the end of the cutter shaft 24, the nose piece 4 is placed on the power source 16 at a predetermined position to permit the wrench to tighten the collet 68, rotating the nose piece 4, if necessary. When the collet 68 is tight, the nose piece 4 is tightened on the power source 16.

Figure 3:
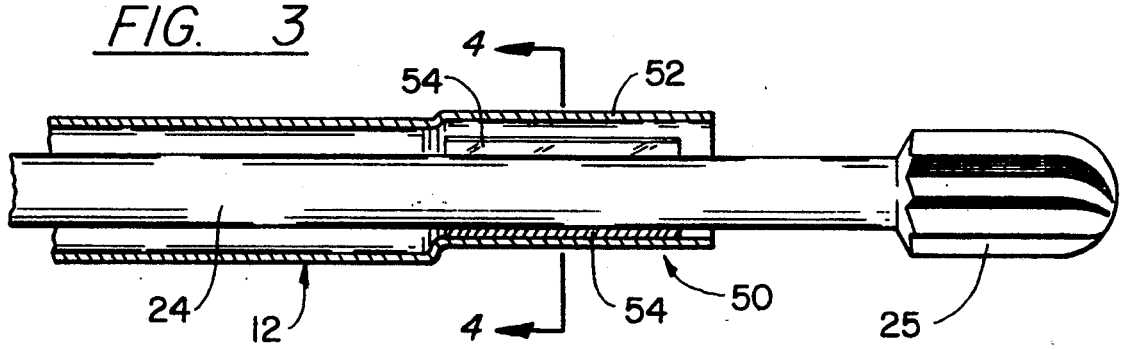
FIG. 3 is an enlarged view of the end of the shaft support tube and cutter shaft with a positive bearing arrangement between the cutter shaft and the free end of the shaft support tube which is formed triangular in shape and which includes fixed bearing members providing bearing contact.
Figure 4:
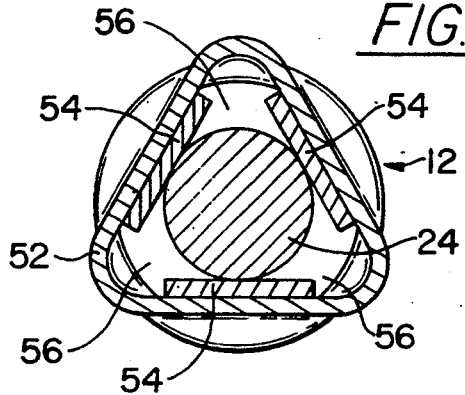
FIG. 4 is a view taken on the line 4—4 of FIG. 3 showing the positive bearing arrangement.

The cutter shaft 24 placed in the shaft support tube 12 extends through the seal 6 into the recess 18 where it can be attached to a power source 16. A positive bearing arrangement 50 supports the cutter shaft 24 at the free end of the shaft support tube 12 adjacent a cutter 25. The free end of the shaft support tube 12, as seen in FIGS. 3 and 4, has its cross-section shaped as a triangular tube 52 with each side spaced from the cutter shaft 24. Bearing plates 54 are fixed on the inner surface of each of the sides of the triangular tube 52 to have line contact with the cutter shaft 24. These bearing plates 54 are members of high density and have a low coefficient of friction. An opening 56 is located where each of the sides of the triangular tube 52 meet. These openings 56 provide for a fluid flow through the shaft support tube 12 for supporting cutter shaft 24 and cooling the cutter 25.

Figure 5:
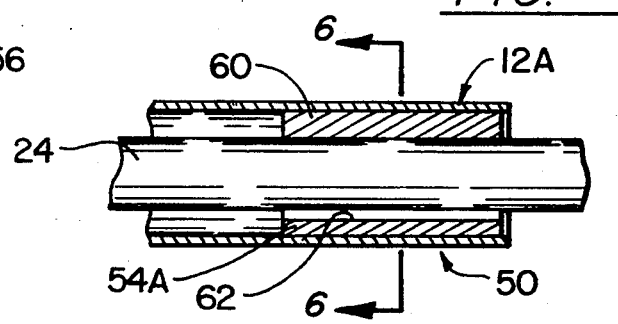
FIG. 5 is a view similar to FIG. 3 of a modified positive bearing arrangement wherein said shaft support tube remains cylindrical with a cylindrical bearing member fixed therein with lands providing bearing contact.
Figure 6:
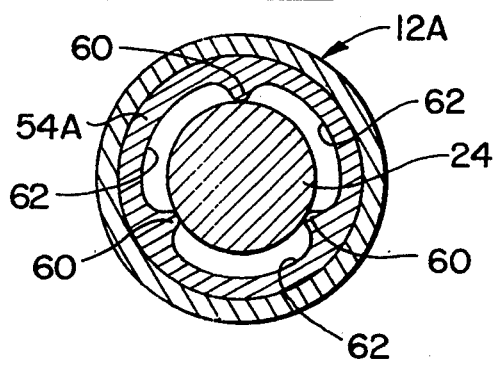
FIG. 6 is a view taken on the line 6—6 of FIG. 5.

The free end of the shaft support tube 12A, as seen in FIGS. 5 and 6, has its cross-section shaped as a cylindrical extension of the support tube. A cylindrical bearing member 54A is placed in the cylindrical end 12A of the shaft support tube 12 around the cutter shaft 24. The cylindrical bearing member 54A has its outer surface fixed within the inner surface of the shaft support tube 12A and the inner surface of the cylindrical bearing member 54A is formed having three bearing lands 60 which engage the outer surface of the cutter shaft 24. Openings 62, formed between the lands 60, provide the supporting and cooling action of openings 56 in FIG. 4. While these lands 60 are longitudinal, they can be formed in a spiral manner as desired.

Figure 7:
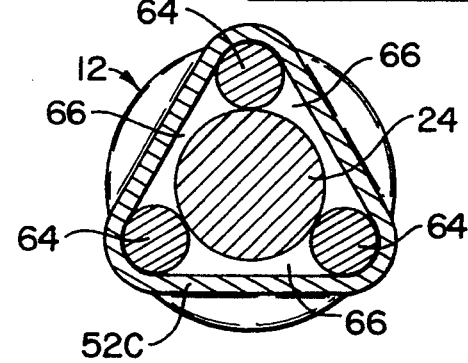
FIG. 7 is a view of a modified positive bearing arrangement using the shaft support tube having the free end of triangular shape, as in FIG. 3, with a fixed bearing cylinder positioned in each corner of the triangular shape.

The free end of the shaft support tube 12, as seen in FIG. 7, has a triangular shape 52C, as shown in FIG. 4. However, in this modification, cylindrical bearing members 64 are positioned to mate in each of the apexes of the triangular tube 52C. It is noted that this arrangement also provides line contact with the cutter shaft 24. It is also noted that openings 66 are located between each of the cylindrical bearing members 64 to provide for fluid flow through the shaft support tube 12 as described above.

The free end of the shaft support tube 12B, as seen in FIGS. 8 and 9, has its cross-section shaped as a cylindrical extension of the support tube 12B with three indentations 70 formed therein to act as bearing members to keep the cutter shaft 24 in the center line of the support tube 12B and prevent whipping. These indentations 70 form openings 72 therebetween to provide for fluid flow through the shaft support tube 12B as described above. The inner surfaces of the indentations 70 can have a coating applied to provide an improved bearing surface. An application of ME-92 can be placed on stainless steel, for example, and increase wear-life while providing a smooth, slippery surface. ME-92 can be obtained from Electrolizing, Inc.

The free end of the shaft support tube 12C, as seen in FIGS. 10 and 11, has its cross-section shaped as a cylindrical extension of the shaft support tube 12C with three cut-out sections 80 equally spaced therearound to each receive a bearing plate 82 extending radially into the interior of the shaft support tube 12C. Each bearing plate 82 rests on the sides of its cut-out section 80 and is contoured to have its outer surface 84 form a continuation of the outer surface of shaft support tube 12C. The inner surfaces 86 of the bearing plate 82 are spaced to form bearing members for the cutter shaft 24. A retaining sleeve 88 on the shaft support tube 12D is slidably placed over the bearing plates 82 and fixed in place. Openings 89 are formed between the cutter shaft 24 adjacent bearing plates 82, and the interior shaft support tube 12C between the bearing plates 82.

The free end of the shaft support tube 12D, as seen in FIGS. 12 and 13, has its cross-section shaped as a cylindrical extension of the shaft support tube 12D with three radial integral projections 90 spaced equally around the inner periphery extending inwardly. A cylindrical bearing 92 is fixed to the projections 90 to receive and support the cutter shaft 24. Openings 96 are formed between the shaft support tube 12D, projections 90, and cylindrical bearing 92 to provide for fluid flow through the shaft support tube 12D as described above.

The bearing material for bearing plates 54, cylindrical bearing member 54A, cylindrical bearing members 64, bearing plates 82, and cylindrical bearing 92, is of high density having a low coefficient of friction. In a surgical drilling instrument 2 designed, as shown in FIG. 4, the bearing plate 54 was designed having a length equal to approximately twice the diameter of the shaft support tube 12, and the material to be used was made of sapphire. Another jewel bearing material which could be used is ruby.

While openings 56, 62, 66, 72, 89, and 96 have been referred to in the six modifications, they direct the liquid passing through the surgical drilling instrument 2 onto the cutter 25. This flow directed onto the cutter 25 (1) cools the cutter; (2) irrigates the area being drilled; and (3) aids in supporting the cutter shaft 24 within the shaft support tube 12. The amount of liquid flowing can be controlled by the pressure of the supply of liquid (and control of opening contour or size).

While the principles of the invention have now been made clear in an illustrative embodiment, it will become obvious to those skilled in the art that many modifications in arrangement are possible without departing from those principles. The appended claims are, therefore, intended to cover and embrace any such modifications, within the limits of the true spirit and scope of the invention.

What is claimed is:

1. A surgical cutting instrument including a nose body, said nose body having a forward end and a rearward end, an opening in said nose body extending through said nose body from said forward end to said rearward end, a shaft support tube having a rearward end extending into the opening from the forward end of said nose body, said shaft support tube having a forward end, means for fixing said rearward end of said shaft support tube in said opening in said nose body, a cutter for cutting, said cutter having a non-cutting drive shaft, said drive shaft extending coaxially through said shaft support tube, an annular passageway being formed between said drive shaft and shaft support tube, said cutter being located forward of the forward end of said shaft support tube, an inlet passageway in said nose body for directing a fluid through said nose body to said opening, a hole in said shaft support tube for directing a fluid from said inlet passageway to said annular passageway, a seal means for sealing is positioned to seal between said drive shaft and said shaft support tube rearwardly of said hole, a bearing means being fixed to said shaft support tube between the forward end of said shaft support tube and said drive shaft, said bearing means providing opening means therethrough, said annular passageway being aligned with said opening means for directing a fluid outwardly therethrough onto said cutter, said bearing means comprises a plurality of inwardly extending projections fixed to said shaft support tube coacting with said drive shaft.

2. A surgical cutting instrument as set forth in claim 1 wherein said projections are indentations around the periphery of the shaft support tube.

3. A surgical cutting instrument as set forth in claim 2 wherein said indentations have inner surfaces, the inner surfaces of said indentations being coated with a medically safe coating to increase wear-life and provide a smooth, slippery surface.

4. A surgical cutting instrument including a nose body, said nose body having a forward end and a rearward end, an opening in said nose body extending through said nose body from said forward end to said rearward end, a shaft support tube having a rearward end extending into the opening from the forward end of said nose body, said shaft support tube having a forward end, means for fixing said rearward end of said shaft support tube in said opening in said nose body, a cutter for cutting, said cutter having a non-cutting drive shaft, said drive shaft extending coaxially through said shaft support tube, an annular passageway being formed between said drive shaft and shaft support tube, said cutter being located forward of the forward end of said shaft support tube, an inlet passageway in said nose body for directing a fluid through said nose body to said opening, a hole in said shaft support tube for directing a fluid from said inlet passageway to said annular passageway, a seal means for sealing is positioned to seal between said drive shaft and said shaft support tube rearwardly of said hole, a bearing means being fixed to said shaft support tube between the forward end of said shaft support tube and said drive shaft, said bearing means providing opening means therethrough, said annular passageway being aligned with said opening means for directing a fluid outwardly therethrough onto said cutter, the forward end of said shaft support tube is formed having a triangular cross-section of three sides, said bearing means including a bearing plate on the inner surface of each side coacting with said drive shaft.

5. A surgical cutting instrument including a nose body, said nose body having a forward end and a rearward end, an opening in said nose body extending through said nose body from said forward end to said rearward end, a shaft support tube having a rearward end extending into the opening from the forward end of said nose body, said shaft support tube having a forward end, means for fixing said rearward end of said shaft support tube in said opening in said nose body, a cutter for cutting, said cutter having a non-cutting drive shaft, said drive shaft extending coaxially through said shaft support tube, an annular passageway being formed between said drive shaft and shaft support tube, said cutter being located forward of the forward end of said shaft support tube, an inlet passageway in said nose body for directing a fluid through said nose body to said opening, a hole in said shaft support tube for directing a fluid from said inlet passageway to said annular passageway, a seal means for sealing is positioned to seal between said drive shaft and said shaft support tube rearwardly of said hole, a bearing means being fixed to said shaft support tube between the forward end of said shaft support tube and said drive shaft, said bearing means providing opening means therethrough, said annular passageway being aligned with said opening means for directing a fluid outwardly therethrough onto said cutter, the forward end of said shaft support tube is formed having a triangular cross-section of three sides and three angular corners, said bearing means including a bearing member in each angular corner coacting with said drive shaft.

6. A surgical cutting instrument including a nose body, said nose body having a forward end and a rearward end, an opening in said nose body extending through said nose body from said forward end to said rearward end, a shaft support tube having a rearward end extending into the opening from the forward end of said nose body, said shaft support tube having a forward end, means for fixing said rearward end of said shaft support tube in said opening in said nose body, a cutter for cutting, said cutter having a non-cutting drive shaft, said drive shaft extending coaxially through said shaft support tube, an annular passageway being formed between said drive shaft and shaft support tube, said cutter being located forward of the forward end of said shaft support tube, an inlet passageway in said nose body for directing a fluid through said nose body to said opening, a hole in said shaft support tube for directing a fluid from said inlet passageway to said annular passageway, a seal means for sealing is positioned to seal between said drive shaft and said shaft support tube rearwardly of said hole, a bearing means being fixed to said shaft support tube between the forward end of said shaft support tube and said drive shaft, said bearing means providing opening means therethrough, said annular passageway being aligned with said opening means for directing a fluid outwardly therethrough onto said cutter, said bearing means includes a jewel bearing material for a bearing surface.

7. A surgical cutting instrument as set forth in claim 6 wherein said jewel bearing material is sapphire.

8. A surgical cutting instrument including a nose body, said nose body having a forward end and a rearward end, an opening in said nose body extending through said nose body from said forward end to said rearward end, a shaft support tube having a rearward end extending into the opening from the forward end of said nose body, said shaft support tube having a forward end, means for fixing said rearward end of said shaft support tube in said opening in said nose body, a cutter for cutting, said cutter having a non-cutting drive shaft, said drive shaft extending coaxially through said shaft support tube, an annular passageway being formed between said drive shaft and shaft support tube, said cutter being located forward of the forward end of said shaft support tube, an inlet passageway in said nose body for directing a fluid through said nose body to said opening, a hole in said shaft support tube for directing a fluid from said inlet passageway to said annular passageway, a seal means for sealing is positioned to seal between said drive shaft and said shaft support tube rearwardly of said hole, a bearing means being fixed to said shaft support tube between the forward end of said shaft support tube and said drive shaft, said bearing means providing opening means therethrough, said annular passageway being aligned with said opening means for directing a fluid outwardly therethrough onto said cutter, said bearing means comprises projection members, cut-out sections being equally spaced around said shaft support tube, a projection member being placed in each cut-out section extending into said shaft support tube to coact with said drive shaft, means fixing said projection members to said shaft support tube.

9. A surgical cutting instrument as set forth in claim 8 wherein each projection member has an inner and outer surface, the inner surface of each projection member rests on the sides of its cut-out section limiting its inward movement, the outer surface of each projection member conforming to the outer surface of the shaft support tube, a retaining cylindrical sleeve is fixed on the shaft support tube around the projection members to hold them in place.

10. A surgical cutting instrument including a body member, said body member having a forward end and a rearward end, a shaft support tube having a rearward end extending into the forward end of said body member, said shaft support tube having a forward end, means for fixing said rearward end of said shaft support tube to said body member, a cutter for cutting, said cutter having a non-cutting drive shaft, said drive shaft extending coaxially through said shaft support tube and into said body member, an annular passageway being formed between said drive shaft and shaft support tube, said cutter being located forward of the forward end of said shaft support tube, an inlet passageway in said body member for directing a fluid through said body member to said annular passageway, a bearing means being fixed on said shaft support tube between the forward end of said shaft support tube and said drive shaft, said bearing means having an opening therethrough, said annular passageway being aligned with said opening for directing a fluid outwardly therethrough onto said cutter, said bearing means comprises a plurality of inwardly extending projections fixed to said shaft support tube coacting with said drive shaft.

11. A surgical cutting instrument including a body member, said body member having a forward end and a rearward end, a shaft support tube having a rearward end extending into the forward end of said body member, said shaft support tube having a forward end, means for fixing said rearward end of said shaft support tube to said body member, a cutter for cutting, said cutter having a non-cutting drive shaft, said drive shaft extending coaxially through said shaft support tube and into said body member, an annular passageway being formed between said drive shaft and shaft support tube, said cutter being located forward of the forward end of said shaft support tube, an inlet passageway in said body member for directing a fluid through said body member to said annular passageway, a bearing means being fixed on said shaft support tube between the forward end of said shaft support tube and said drive shaft, said bearing means having an opening therethrough, said annular passageway being aligned with said opening for directing a fluid outwardly therethrough onto said cutter, the forward end of said shaft support tube is formed having a triangular cross-section of three sides, said bearing means including a bearing plate on the inner surface of each side coacting with said drive shaft.

12. A surgical cutting instrument including a body member, said body member having a forward end and a rearward end, a shaft support tube having a rearward end extending into the forward end of said body member, said shaft support tube having a forward end, means for fixing said rearward end of said shaft support tube to said body member, a cutter for cutting, said cutter having a non-cutting drive shaft, said drive shaft extending coaxially through said shaft support tube and into said body member, an annular passageway being formed between said drive shaft and shaft support tube, said cutter being located forward of the forward end of said shaft support tube, an inlet passageway in said body member for directing a fluid through said body member to said annular passageway, a bearing means being fixed on said shaft support tube between the forward end of said shaft support tube and said drive shaft, said bearing means having an opening therethrough, said annular passageway being aligned with said opening for directing a fluid outwardly therethrough onto said cutter, said bearing means comprises projection members, cut-out sections being equally spaced around said shaft support tube, a projection member being placed in each cut-out section extending into said shaft support tube to coact with said drive shaft, means fixing said projection members to said shaft support tube.

* * * * *